United States Patent [19]

Lever et al.

[11] Patent Number: 5,209,733
[45] Date of Patent: May 11, 1993

[54] CONTAMINATED SYRINGE GUARD WITH FLEXIBLE ASTERISK APERTURE

[76] Inventors: Peter G. Lever, 3329 Oak Dr., Hollywood, Fla. 33021; Helen T. Whitehouse, 18125 NW. 5th Ct., Miami, Fla. 33169

[21] Appl. No.: 895,994

[22] Filed: Jun. 8, 1992

[51] Int. Cl.$^5$ .................. A61M 5/50; A61M 5/32; B65D 83/10
[52] U.S. Cl. .................. 604/110; 206/366; 604/192
[58] Field of Search ............... 604/110, 192, 198, 263; 206/363–367

[56] References Cited

U.S. PATENT DOCUMENTS

| | | | |
|---|---|---|---|
| 1,050,043 | 1/1913 | Sellar | 206/366 X |
| 2,467,678 | 4/1949 | Lockhart | 206/366 |
| 3,876,067 | 4/1975 | Schwarz | 206/205 |
| 4,742,910 | 5/1988 | Staebler | 206/365 |
| 4,767,412 | 8/1988 | Hymanson | 604/192 |
| 4,892,522 | 1/1990 | Suzuki et al. | 604/192 |
| 4,986,817 | 1/1991 | Code | 604/192 |
| 5,000,742 | 3/1991 | Morrison | 604/192 |
| 5,039,004 | 8/1991 | Simpson | 229/132 |
| 5,097,950 | 3/1992 | Weiss et al. | 206/366 |
| 5,098,404 | 3/1992 | Collins | 604/199 |
| 5,152,394 | 10/1992 | Hughes | 206/366 |
| 5,158,558 | 10/1992 | Melker et al. | 604/111 |

FOREIGN PATENT DOCUMENTS 0295888 12/1988 European Pat. Off. ............ 604/263

Primary Examiner—John D. Yasko
Assistant Examiner—Adam J. Cermak
Attorney, Agent, or Firm—Robert J. Van Der Wall

[57] ABSTRACT

Disclosed is an apparatus and method to protect medical care workers from accidental needle sticks with syringe needles that have been contaminated by blood or other body fluids, such as after use on a patient. The device renders the syringe readily disposable with minimal risk and itself is intended to be discarded in locked configuration with the contaminated syringe. The apparatus is comprised of a hollow cylinder of a hard material. The cylinder is preferably fabricated to have a circular cross-section. The device preferably contains a recess on at least one of the substantially circular ends. Disposed at the lowest portion of the recess is an asterisk aperture comprised of points generated by the intersection of adjoining radially disposed cuts, which cuts radiate outward toward, but not reaching, the periphery of the end which intersects with the cylindrical surface. Each of the points about the circumference of the asterisk aperture will flex when a needle is inserted into the aperture so far that the hub of the needle between said needle and the syringe body is also inserted. The points engage the hub thereby locking and preventing withdrawal of the hub from the inventive device after insertion. Also disposed within the device substantially adjacent each asterisk aperture is a substantially circular seal preferably fabricated from a soft rubber or plastic material such that the seal may be readily penetrated by the needle but which will prevent discharge of any fluid escaping from the syringe after the same has been inserted.

4 Claims, 1 Drawing Sheet

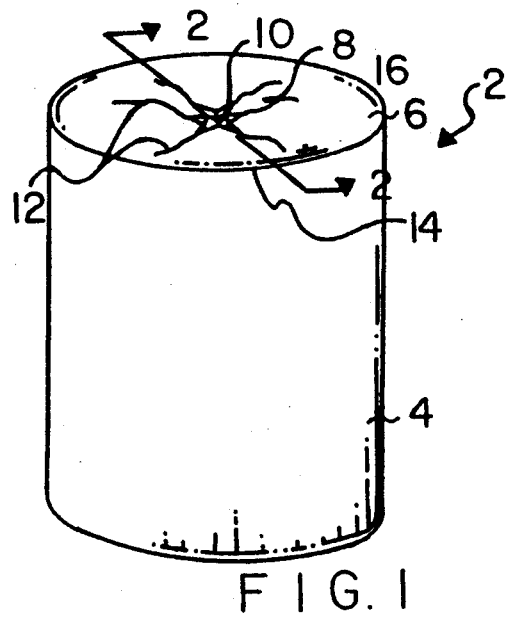
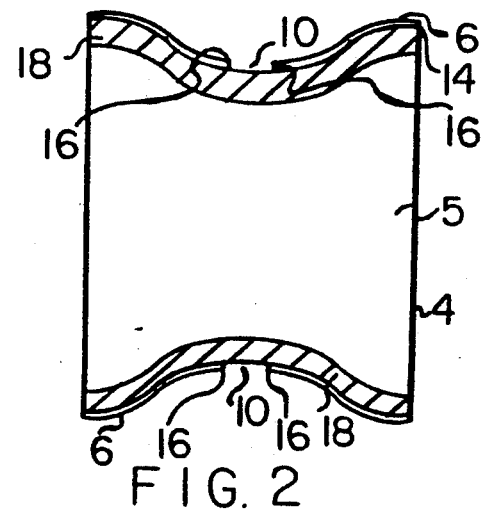
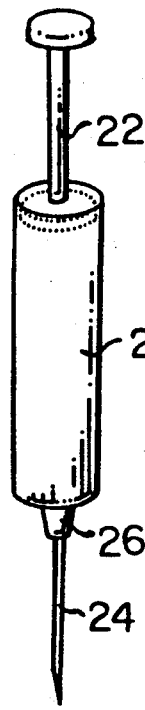
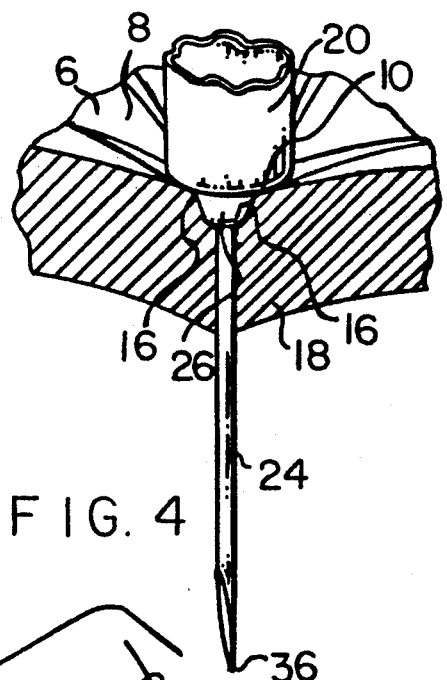
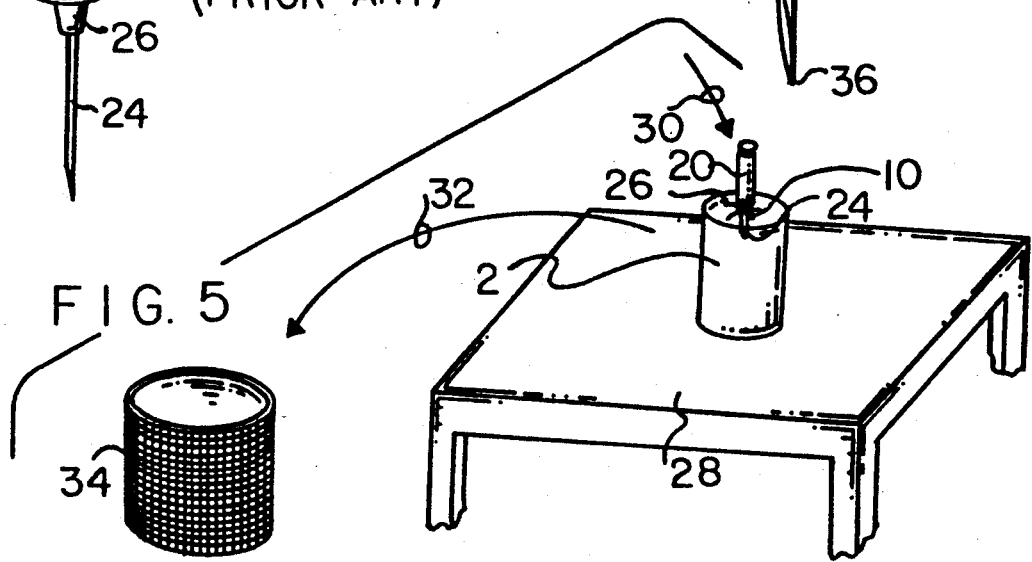

CONTAMINATED SYRINGE GUARD WITH FLEXIBLE ASTERISK APERTURE

FIELD OF THE INVENTION

The present invention relates to the field of medical equipment and, more particularly, to a device for protecting medical care workers from accidental needle sticks with syringe needles that have been contaminated by blood or other body fluids after use on a patient. The device renders the syringe readily disposable with minimal risk and itself is intended to be discarded with the contaminated syringe.

BACKGROUND OF THE INVENTION

The epidemic of Acquired Immune Deficiency Syndrome (AIDS) has greatly intensified the concern among the medical community of the accidental infection of health care workers by contaminated body fluids. Of course the problem existed prior to the spread of AIDS because of the risk of contracting hepatitis viruses, venereal diseases, and other infectious agents from such things as accidental needle stick injuries. Nevertheless, the fatality rate with AIDS and uncertainty, at least in the early years, of the means of infection and probability of contracting the disease upon exposure to contaminated body fluids has given rise to a virtual explosion of inventive activity directed to minimizing the risks to health care workers occupationally exposed to those being treated for AIDS or which may carry, without their own knowledge, the Human Immunodeficiency Virus (HIV) which causes AIDS.

The problem is not only the relatively modest statistical risk of a health care worker contracting AIDS or AIDS-Related Complex. It is also the economic cost of repeated testing of and psychological impact to the many health care workers who are directly exposed to contaminated body fluids through various relatively common accidents that occur in health care facilities notwithstanding the increased attention paid by exposed personnel. In addition to the inventive activity above described, there have been a number of published studies investigating the nature of accidents whereby health care workers are exposed to contaminated body fluids. These have determined that the overwhelming majority of such injuries are caused by accidental needle sticks or other sharp object injuries, but there are also included mucous membrane splashes and contamination of open wounds. There is, for example, one instance where there was minimal cutaneous blood exposure to a health care worker had chapped hands at the time of contact and thereafter contracted the HIV. In one study published by Jagger in The New England Journal of Medicine on Aug. 4, 1988, entitled *Rates of Needle-Stick Injury Caused By Various Devices in a University Hospital*, it was determined that disposable syringes accounted for thirty-five (35%) percent of needle stick injuries, prefilled cartridge syringes for twelve (12%) percent, winged steel-needle sets for seven (7%) percent, phlebotomy needles for five (5%) percent and intravenous catheter stylets for two (2%) percent, with all other devices accounting for thirteen (13%) percent.

Much of the inventive activity appears to be directed toward development of syringes which can be recapped or otherwise protected following contamination without any movement of the health care worker's hand in the direction of the point of the needle. Of course, there was substantial prior art where that particular criterion was not a factor, some of which appears to have predated the concern caused by the AIDS epidemic.

Some of the criteria that bear on the question of the practical value of any modification of prior art health care practices follow. These include a simple and inexpensive device with uncomplicated usage, extremely low manufacturing and selling costs, a design which minimizes the need for the retraining of health care workers, little or no user assembly, fast and convenient use, the absence of a need to cover the needle using a motion that passes the user's hand toward the point of the needle, a device that does not require the health care worker to be exposed to hazardous conduct in employing same, and a safety feature that remains in effect after disposal thereby protecting trash handlers.

The prior art includes a number of interesting references. Several were directed to shielding of syringes for radioactivity, i.e., those directed to protection of health care workers, exposure to radioactive medications, or agents contained in a syringe. The first of these was Collica, et al., U.S. Pat. No. 4,060,073, which included a slot for transparent radiation shielding for a transparent radiation shielding window so that the health care worker can observe the location of the syringe plunger.

Another reference teaching a protective shielding assembly for use with a syringe incorporating radioactive material is Larrabee, U.S. Pat. No. 3,993,063. This reference teaches radioactive shielding in the form of a container in which is disposed a vial of radioactive medication or other material and a syringe, each disposed in a portion which is slidable with respect to the other so as to permit the needle of the syringe to penetrate the septum of the vial for withdrawing into the syringe the medication or other material.

A further reference is U.S. Pat. No. 4,564,054 issued to Gustavsson for a fluid transfer system which includes accordion sidewalls and several membranes for the purpose of preventing air contamination when transferring a substance from one vessel to another, the latter frequently a syringe. The accordion sidewall construction is a substitute for the slidable portions of the preceding reference, even though the purposes of the two are dissimilar. The latter reference includes numerous embodiments, however, none of them teach or suggest the present invention.

One of the references that predates the AIDS epidemic is a device and technique for minimizing risk of contamination by a blood sample patented by Bordow, U.S. Pat. No. 4,085,737, which includes a cap for a syringe needle with a vacuum chamber to purge air and some blood. This reference is ineffective to protect against needle sticks because it actually requires movement of the cap toward the needle and some force to be applied to cause penetration of a fluid impervious seal disposed interiorly of the device.

As indicated above, a number of references have been patented in response to the AIDS epidemic and crisis among health care workers and attempt to protect the latter from accidental needle stick injuries. One of these is Luther, U.S. Pat. No. 4,747,836, which teaches a needle guard and assembly having a sleeve which rotates in a spiral slot to extend over the needle. When opened, the guard pivots out of the way.

Another reference of some interest is the patent issued to Spencer for a sheathed syringe, U.S. Pat. No. 4,723,943, which teaches a slidable sleeve disposed about the syringe and which can be extended by motion away from the point of the needle to protect against accidental needle sticks. The sheath is rotated in one direction for temporary extension and is rotated in another direction for extension that is locking and prevents further retraction. The device allows either re-use or protection for disposal but requires alignment and particular care of the health care worker in its use. Spencer also suffers from the expensive limitation that one such device is needed for each syringe, and requires different dimensions for each different size syringe.

A similar inventive purpose is apparent in the invention of Masters, et al. for a syringe with a safety sheath, U.S. Pat. No. 4,681,567. It teaches a slidable sheath which locks into position when extended and can also be operated without motion of a health care worker's hand toward the point of the syringe needle.

Another reference is the invention of Alvarez for a retractable syringe needle cover that has a locking means, U.S. Pat. No. 4,139,009. Alvarez teaches a plurality of elastically resilient arms surrounding the syringe needle attached to an annular slide member which surrounds the needle and slides with respect to said needle by flexure of the resilient arms. Locking is achieved by movement of a slidable locking ring about the central portion of the resilient arms. One additional reference is the McDonald Safe Guard Needle described in a medical technology article on pp. 120,21 of the Oct. 23, 1989 issue of *Design News*. This invention utilizes a shield tube that automatically extends when the needle is pulled from a catheter, with which the device is intended for use.

SUMMARY OF THE INVENTION

Bearing in mind the foregoing, it is a principal object of the present invention to provide a contaminated needle protection device which is simple and inexpensive to manufacture and sell.

It is a correlated object of the invention to provide such a device that is susceptible to fast and convenient use having no user assembly.

Another object of the invention is to provide a device which is disposable with and connected to the disposable syringe so that both are discarded together.

A related object of the invention is to provide such a device wherein the connection between the disposable syringe and the inventive device is locking such that the two devices cannot readily be separated except with the exertion of great force. This feature provides great protection following contamination.

Another related object of the invention is to provide a device which includes internal seals preventing leakage of contamination from inventive device, thereby providing protection in the event that fluids contained within the protective device are diluted by medication remaining within the syringe, and which is forced therefrom by accidental further pressure applied to the plunger of the syringe by the trash disposal process.

An additional object of the invention is to provide a contaminated syringe guard which does not either require recapping of the needle nor any other motion in which the hand of the user must travel in the direction of the point of the needle.

A related object of the invention is to provide such a device that does not require the health care worker to be exposed to hazardous conduct in employing the same.

A further object of the invention is to provide a device which also protects trash handlers after disposal of the device and connected contaminated syringe.

One more object of the invention is to provide such a device which is light weight and compact in size so that the same can be carried in a reasonable quantity by any health care worker using a disposable syringe likely to be exposed to contaminated body fluids. That is, a shop coat pocket full of the inventive devices can be carried by, for example, a registered nurse or doctor who can utilize the same immediately after withdrawing the needle of the syringe from the patient.

Another object of the invention is to provide a method of use of the device which materially contributes to the objective of maximizing protection against accidental needle sticks.

Other objects and advantages will be apparent to those skilled in the art upon examination of the following descriptions and the appended drawings.

In accordance with the major aspect of the invention, there is provided a device comprising a hollow cylinder of a hard material, such as a metal can. The cylinder preferably is fabricated having a circular cross-section. The device preferably contains a recess on both of the substantially circular ends. Disposed at the lowest portion of the recess in a substantially central position of each end is an aperture with cuts through the end radiating outward toward, but not reaching, the periphery of the end which intersects with the cylindrical surface. This aperture will be termed an asterisk aperture because of its resemblance to that symbol. Each of the points generated by the intersection of adjoining radially disposed cuts will flex when a needle is inserted into the aperture so far that the hub of the needle between said needle and the syringe body is also inserted. These points then engage the hub, thereby preventing withdrawal of the hub from the inventive device after insertion. Disposed within the cylindrical device substantially adjacent each of the circular ends is a substantially circular seal preferably fabricated from a soft rubber or plastic material such that said seal may be readily penetrated by the needle, but which will prevent discharge of any fluid escaping from the syringe after the same has been inserted.

In accordance with another aspect of the present invention, there is provided a recommended method of use in which the inventive device is placed upon a flat surface and the needle stuck into either end with only the hand holding the contaminated syringe employed. Once the needle is stuck into the device and locked therein by the points of the asterisk aperture, the combination is disposed of in the conventional manner for disposable syringes, and the needle and contaminants trapped within the contaminated syringe guard are never exposed to humans again, thereby protecting trash handlers as well as any other health care workers thereafter exposed to the contaminated syringe and connected contaminated syringe guard.

The invention will be better understood upon reference to the appended drawings in which:

BRIEF DESCRIPTION OF DRAWINGS

FIG. 1 is a perspective view of the inventive device.

FIG. 2 is a cross-sectional view taken along the line 2—2 of FIG. 1.

FIG. 3 is a view of a typical prior art disposable syringe.

FIG. 4 is an enlarged broken cross-sectional view showing the insertion of the hub of the disposable syringe into the asterisk aperture at the center of either end of the inventive device of FIG. 1, particularly illustrating engagement of the points with said hub.

FIG. 5 illustrates the method of use of the inventive device in which the inventive device is placed on a table or similar surface, the inventive device receives the needle point and hub of the disposable syringe, locks the same, and the combination is then disposed of in a medical waste container.

DETAILED DESCRIPTION OF THE PREFERRED EMBODIMENTS

FIG. 1 is a perspective view of the inventive contaminated syringe guard 2 comprised of a cylindrical wall 4 and an upper end 6. Upper end 6 is symmetrical with the opposite end not visible in figure as hereinafter described. End 6 is preferably circular, and in which is disposed a recess 8 at the bottom of which is an asterisk aperture 10. The same is surrounded by radial cuts 12 extending toward the end periphery 14 which represents the intersection between the end 6 and the cylindrical wall 4. Each of the radial cuts 12 terminates at the asterisk aperture 10 with an aperture point 16. Cylindrical wall 4 and ends 6 are preferably fabricated from a hard material such as sheet metal.

FIG. 2 is a cross-sectional view taken along the line 2—2 of FIG. 1. In this view it is seen that the end 6 is a mirror image of a similar end 6 disposed at the lower end such that the device is substantially symmetrical. Disposed within the cylindrical wall 4 in a cavity 5. Further, in proximity to each end 6 is a seal 18 which is preferably fabricated from a sufficiently soft material that a hypodermic needle will readily penetrate it, but which will prevent fluid from escaping through the asterisk aperture 10. Also seen in FIG. 2 are aperture points 16.

FIG. 3 illustrates a typical prior art disposable syringe 20 showing the syringe plunger 22 in the extended position. Also seen is needle 24 which is connected to the syringe 20 by hub 26.

FIG. 4 is an enlarged broken perspective cross-sectional view showing the insertion of hub 26 into asterisk aperture 10 which is disposed in recess 8 of partially broken end 6 seen in perspective. This figure particularly illustrates engagement of hub 26 by aperture points 16 in a manner which prevents withdrawal of hub 6 because of the downward engaging direction of aperture points 16 after insertion of hub 26. Also seen in cross-sectional view is the penetration of seal 18 by needle 24 in close fitting arrangement to avoid leakage of any fluid that escapes from the distal end 36 of needle 24.

FIG. 5 illustrates the method of use of the inventive apparatus in a schematic format. A contaminated syringe guard 2 is placed on a table 28 or other substantially horizontal surface. A contaminated syringe 20 is placed into contaminated syringe guard 2 by a downward motion as illustrated by arrow 30. At this point it should be noted that the contaminated syringe 20 may be held above the needle 24 shown in phantom view inside contaminated syringe guard 2. Since the contaminated syringe guard 2 will stand on a horizontal surface without any other support, this downward motion 30 need not direct contaminated needle 24 toward any portion of the health care worker's body. It is then thrust into asterisk aperture 10 such that hub 26 is engaged with aperture points 16 as was illustrated in FIG. 4. Also as shown in FIG. 4, it may not thereafter be readily removed because of the orientation of the aperture points 16 therein illustrated. The combination of the contaminated syringe 20 and contaminated syringe guard 2 is thereafter thrown in a disposal motion 32 toward a medical waste container 34. Subsequent health care workers or trash handlers coming in contact with the combination of contaminated syringe 20 and contaminated syringe guard 2 are protected from exposure to contaminated needle 24 or contaminated body fluids therein contained including particularly by reason of seal 18 as illustrated in FIGS. 2 and 4.

Having described the presently preferred embodiments of the invention, it should be understood that various changes in construction and arrangement will be apparent to those skilled in the art and fully contemplated herein without departing from the true spirit of invention. Accordingly, there is covered all alternatives, modifications and equivalents as may be included within the spirit and scope of the invention as defined in the appended claims.

We claim:

1. A contaminated syringe guard comprising:

a cylindrical wall;

ends attached about their periphery to the cylindrical wall, forming a cavity with the cylindrical wall and between the ends and at least one end including a recess disposed in a substantially central position in the end;

an asterisk aperture disposed in at least one end at a base of the recess, which aperture is comprised of a plurality of cuts in the end radiating outward from the aperture and extending toward, but not reaching, the periphery of the end wherein the cuts terminate in proximity to the asterisk aperture in aperture points which are adapted to flex downwardly when a syringe needle hub is inserted into the asterisk aperture thereby lockingly engaging the syringe needle hub; and a seal disposed within the cavity in proximity to the asterisk aperture, said seal being adapted to be readily penetrated by a syringe needle, but resisting leaks of fluid from within the cavity after penetration by the needle.

2. The guard of claim 1 in which an asterisk aperture is disposed in both ends.

3. A method of guarding against accidental needle sticks from a syringe contaminated with body fluids comprising:

placing a contaminated syringe guard on a substantially horizontal surface in a configuration where an end is directed upward;

grasping a contaminated syringe by a plunger end away from the contaminated needle;

moving the contaminated syringe needle away from any portion of any body and toward and asterisk aperture having a plurality of flexible aperture points disposed about a circumference of the asterisk aperture and disposed in at least one end of the contaminated syringe guard;

directing the contaminated syringe needle in a downward motion into the asterisk aperture;

inserting the contaminated syringe into the asterisk aperture far enough so that a needle hub disposed between the needle and the syringe flexes the aperture points in a downwardly engaging direction and lockingly engages the needle hub with the downwardly engaging aperture points;

picking up a combination of the contaminated syringe and contaminated syringe guard;

directing said combination in a disposal motion toward a medical waste container; and placing said combination in the medical waste container.

4. The method of claim 3 which further comprises placing the contaminated needle into the asterisk aperture a sufficient distance that a point of said needle penetrates a seal disposed within a cavity contained in proximity to the asterisk aperture, said seal being adapted to resist leakage of fluid from within the cavity after penetration by the needle.

* * * * *